United States Patent [19]

Davidson

[11] Patent Number: 5,358,529
[45] Date of Patent: Oct. 25, 1994

[54] PLASTIC KNEE FEMORAL IMPLANTS

[75] Inventor: James A. Davidson, Germantown, Tenn.

[73] Assignee: Smith & Nephew Richards Inc., Memphis, Tenn.

[21] Appl. No.: 27,000

[22] Filed: Mar. 5, 1993

[51] Int. Cl.⁵ ............................................. A61F 2/38
[52] U.S. Cl. ....................................... 623/20; 623/18
[58] Field of Search ..................... 623/16, 18, 20, 22, 623/23

[56] References Cited

U.S. PATENT DOCUMENTS

| | | | |
|---|---|---|---|
| 3,688,316 | 9/1972 | Lagrange et al. | 3/1 |
| 3,868,730 | 3/1975 | Kaufer et al. | 3/1 |
| 4,034,418 | 7/1977 | Jackson et al. | 3/1.911 |
| 4,268,920 | 5/1981 | Engelbrecht et al. | 3/1.911 |
| 4,355,429 | 10/1982 | Mittelmeier et al. | 3/1.911 |
| 4,596,734 | 6/1986 | Kramer | 428/213 |
| 4,923,550 | 5/1990 | Kramer | 156/242 |
| 5,021,061 | 6/1991 | Wevers et al. | 623/20 |
| 5,123,927 | 6/1992 | Duncan et al. | 623/20 |
| 5,181,924 | 1/1993 | Gschwend et al. | 623/20 |

Primary Examiner—David Isabella
Attorney, Agent, or Firm—Pravel, Hewitt, Kimball & Krieger

[57] ABSTRACT

A knee prosthesis includes plastic femoral and metallic (or ceramic) tibial components. The plastic femoral knee component articulates against a polished metal (e.g. cobalt alloy, titanium alloy, or stainless steel), or preferably ceramic (e.g. alumina, zirconia, nitride, or boride) patella and tibial components in a total knee implant. The polymer femoral material can be of a polymer such as ultra high molecular weight polyethylene, or a polymer blend or a fiber or particle reinforced polymer, or layered polymers.

44 Claims, 1 Drawing Sheet

PLASTIC KNEE FEMORAL IMPLANTS

BACKGROUND OF THE INVENTION

1. Field Of The Invention

The present invention relates to surgical prosthetic devices and more particularly to an improved orthopedic knee implant that includes a polymeric femoral component, preferably of an ultra high molecular weight polymeric material that articulates against metallic (or ceramic or ceramic coated metal) patella and tibia components.

2. General Background

About ten years ago, total knee arthroplasty became a popular and routinely accepted treatment for arthritic and other diseases of the knee. During this period of time and before, various combinations of articulating materials were tried with varying degrees of success. Polyacetyl type of polymeric material has been used for the femoral surface and articulating against another polymeric material (e.e. teflon) on the tibial surface. Polymer-polymer articulation has been tested but produced excessive wear. The most widely accepted combination used at present is a metal femoral surface articulating against polymer tibial and patella surfaces.

As the nature of the complex knee joint articulation became better understood, the system most widely used today, a cobalt alloy femoral surface and an Ultra High Molecular Weight Polyethylene (UHMWPE) tibial and patella surface became the standard. However, bioengineers, surgeons, and other scientists are still learning more about the performance of this knee system as sufficient numbers of patients are just now reaching more than ten years postop. In the past five years or so the medical community has come to appreciate the adverse effect of UHMWPE wear debris and its ability in sufficient volume to produce bone lysis and thus revision of the implant.

The most prevalent source of UHMWPE wear debris results from relatively rapid (compared to the tibial surface) wear of the UHMWPE patella surface. If the patella has a metal backing, this backing can eventually wear against the metal femoral surface following excessive polyethylene wear, and further aggravate the wear process and accelerate the adverse consequences via production of metal and UHMWPE debris.

Tibial wear of the UHMWPE has also been observed. Thinner UHMWPE surfaces on the tibia may allow eventual wear through to the underlying metal. Thicker tibial UHMWPE surfaces are desired but at the expense of excessive resection of the bone (tibia) during surgery. In just the past few years, the benefit of ceramic-UHMWPE wear combinations in the total hip joint and in laboratory tests have shown this wear combination to reduce friction and UHMWPE wear. Knee simulator tests in Japan have shown this to also be the case for monolithic ceramic knee femoral components articulating against UHMWPE.

Although the ceramic femoral surfaces show a clear advantage over cobalt alloy femoral surfaces in reducing UHMWPE wear, the fact remains that both the UHMWPE tibia and particularly the UHMWPE patella component (roughly twice the contact stress of the tibial surface) still wear at a finite rate. Alternative attempts to minimize UHMWPE tibial wear include the use of movable tibial segments such as in meniscal bearing total knee designs.

In all the currently available total knee systems both tibial and patella wear of the UHMWPE material occurs against the polished metal femoral surface. During wear of the knee, it is the UHMWPE which undergoes wear in a constant area, such as the domed patella surface, or in a relatively constant area such as in the tibial surface. That is, the wear of the UHMWPE is not minimized because a particular region(s) of the UHMWPE remains in contact with the mating metal surface during relative motion (sliding distance) of the metal surface; The wear factor K, of UHMWPE articulation against polished metal implant surfaces is the volume ($mm^3$) of UHMPE per unit stress and sliding distance. Thus, for a given load (contact stress), reducing the sliding distance over which the metal surface rubs the UHMWPE will reduce the volume of UHMWPE wear debris. The use of both a polymer femoral and tibial and patella component does not eliminate this wear difference and, depending on the polymer combination, may actually increase wear dramatically.

SUMMARY OF THE PRESENT INVENTION

By reversing the material used for the femoral component with that of the patella and tibial components, several advantages occur. First, the wear volume will be less because the location of peak contact area (peak stress) of the UHMWPE (femoral surface) will vary during articulation. Therefore the relative travel distance between the peak stress UHMWPE area and the harder counter bearing surface will be reduced. For example with the pate 1 la button made of UHMWPE, the particular high-stressed dome tip is under constant load as it travels roughly half an inch (under load) against a cobalt alloy femoral surface. However, if the patella button is metal or ceramic, and the femoral component is polyethylene, then the peak stress does not stay in the same UHMWPE location (now the femoral) during the same sequence of motion. Therefore the damage and wear of the UHMWPE for a given activity is spread out and reduced.

Another advantage of using a polymer femoral component is that less resection of the tibia will be required during surgery. Better bone stock and support can thus be maintained for the tibial surface. Likewise, the patella button will require less resection. Moreover, a polymeric femoral component will better transfer load to the underlying bone compared to stiff metal or ceramic femorals components.

Finally, with a polymer femoral component articulating against a metal or ceramic tibial and patella component, only one (rather than two) of the total knee components will be subjected to any significant wear. Should revision surgery be required, only one component may require replacement.

Unlike the early unsuccessful attempts to use both a polymer femoral and tibial component, the use of only a polymer femoral component articulating against a metal or ceramic tibial (and patella) component will reduce polymer wear and friction. Polymer-polymer wear couples do not necessarily provide both low friction and wear during articulation in lubricating mediums. Wear and friction of appropriate metal-polymer and ceramic-polymer wear couples can produce lower levels of friction and wear, and is thus the preferred combination in total knee (and hip) arthroplasty. Further, environmental degradation resistance must be sufficient, particularly against attack by lipids and oxidants.

The present invention provides a polymer (such as UHMWPE) knee femoral component articulating against a polished metal (i.e., cobalt alloy) or preferably ceramic (i.e., alumina, zirconia, nitrides, or borides) patella and tibial components in a total knee implant. The polymer femoral material can be polymers other than UHMWPE or can also be any suitable polymer blend, or fiber-reinforced or particle-reinforced polymer, or layered polymers with appropriate strength, creep, wear resistance, and friction when articulated against metal or ceramic counter bearing surfaces of the patella and tibial component. Further, the polymer must be suitably resistant to environmental degradation (particularly by oxidation, fats, and lipids).

The polymer femoral component can be cemented directly to the femoral resections made during surgery or may incorporate the use of metal or other more rigid backing (full or partial) to enhance cement fixation and wear resistance of the polymer wear surface, or to allow for a surface texture or porous metal bead or mesh coating to be applied for bone ingrowth fixation. The polymer femoral component can also have a porous polymer surface to allow for bone ingrowth or a porous metal mesh surface attached directly for bone ingrowth.

The mating patella and tibial components can be existing implant metals such as cobalt alloy, titanium alloy, or stainless steel with an appropriate polished surface for articulation against the polymer femoral component surface. Surface roughness (Ra) should be less than about 0.05 micron. The patella and tibial components can also be made of other alloys such as these of zirconium, tantalum, and niobium, or these and existing metals with a protective, hard, inert, ceramic coating or other surface hardening treatment such as ion-implantation internal oxidation, gas diffusion hardened carbonization nitriding, etc. Further, the tibial or patella components can be made of solid (monolithic) ceramic such as alumina, zirconia, or silicon carbide.

The preferred embodiment of the apparatus of the present invention provides a metal-backed UHMWPE or other appropriate low wear, high strength (and creep resistance) high degradation resistant, low friction polymer or poller blend knee femoral component articulating against a polished cobalt alloy or ceramic (or ceramic coated metal) patella and tibial knee component.

Generally, in prior art devices the femoral component is made of metal or a metal alloy such as Co-Cr-Mo Alloy. The tibial and patella components are made of plastic or polymer at least with respect to the portions subject to friction and wear.

An example of a patent relating to knee prosthetic devices is U.S. Pat. No. 3,688,316 which describes a prosthetic knee joint in which the femoral component has a polymeric bearing surface and the tibial portion is made from metal. The prosthetic knee joint is formed of a polymeric bearing member, with an upstanding shank received in the femoral shaft, and a metallic rocking member inserted into the tibia. The rocking member having a stem with a disc below the bearing member abutting the tibia, is pivotally supported with the aid of a transverse pin in the bearing member which is partly out away at the rear to permit a relative swinging of the two members over an arc of about 120°. The present invention does not describe such a constrained hinge-type knee and which does not consider critical wear issues associated with current total knee designs in which each of the three knee components is replaced with artificial materials.

U.S. Pat. No. 4,034,418 describes a prosthesis in which the femoral component members are formed from a hard plastic material and the tibial portion has a highly polished metal upper surface. The femoral component is in two pieces and not bridged. The artificial knee joint of the '418 patent is for surgical implantation into a knee and comprises at least one femoral component of hard plastic material and at least one tibial member having a highly polished metal upper surface. Each femoral member is received in a groove cut in the condyle of the femur, and its rear end face, constituting the inferior surface of the femoral member bears against the upper surface of the tibial member. The inferior surface is arcuate polycentered in the sagittal plane and arcuate in the coronal plane. The superior surface of the femoral member has three different planar portions angularly disposed to one another, for load bearing purposes and three different angles of flexion of the knee. However, in this patent, the femoral component is not bridged nor does it describe a total knee prosthesis in which the component replaces bone surface on the more wear-critical anterior portion of the knee femoral region. Further, this patent does not describe a total knee in which the patella is replaced to articulate against the anterior portion of the femur as described in the present invention, and which is a critical wear region as described earlier.

U.S. Pat. Nos. 4,596,734 and 4,923,550 (both assigned to B.F. Goodrich) relate to forming a composite of a metal support, an elastomer and a hard wearing surface formed from ultra-high molecular weight polyethylene. U.S. Pat. Nos. 3,868,730, 4,268,920, and 4,355,429 relate to knee prostheses in which the tibial tray component holds a bearing surface formed from high molecular weight either metal or ceramics. This is in contrast to the present invention in which the knee femoral is described as made of a polymer surface (as opposed to metal or ceramic).

A more recent patent (U.S. Pat. No. 5,021,061) issued to Wevers and Rudan describes a polymer knee femoral insert component, but in which the femoral component portion articulating against the tibia (polyethylene) is metal. The polyethylene insert is fixed to the anterior region of the two-component knee femoral for articulation against the metal patella. The present invention describes a non-modular knee femoral of a suitable polymer bearing material to minimize wear of both the patella and tibial components, versus just the patella component as described in the Wevers and Rudan patent.

A cemented polyethylene femoral component was manufactured several years ago. However, the anterior groove on the femoral component was a deep notch shape and not the shape of the natural femur in the region. Further, this device was thin (less than about 6 mm) and simply cemented to the femur without any metal backing. Thus, the combination of high contact stress within the anterior "V"-shaped groove of the thin femoral component, and the inability for the thin component to maintain proper rigidity resulted in unacceptable clinical results. The present invention describes a more naturally designed femoral and patella geometry, similar to that of the original, intact knee, and which is popular in design for the majority of total knee systems in the market today. Further, the minimum polymer bearing thickness is greater than about eight millimeters (8 mm) to assure proper rigidity and support, and to minimize contact stress in the polymer femoral component and thus minimize polymer wear.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
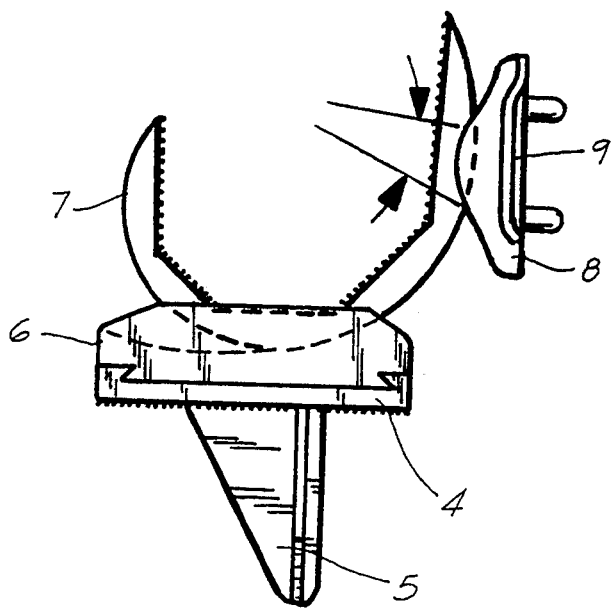
FIG. 1 is a side view of a prior art total knee prosthesis with angulation more typical of a portion of the walking cycle.

FIG. 1 illustrates a prior art total knee prosthesis having a metallic tibial component 4 with a fixation component 5, A polymer insert 6 (such as an ultra high molecular weight polyethylene) is secured on top of the metal tibial component 4. A metallic femoral component 7 has an articulating surface portion that bears against a corresponding articulating surface portion of the polymer insert 6, A polymeric patella component 8 also provides an articulating surface with the metallic femoral component 7, The plastic patellar component can have a metallic backing portion 9.

Figure 2:
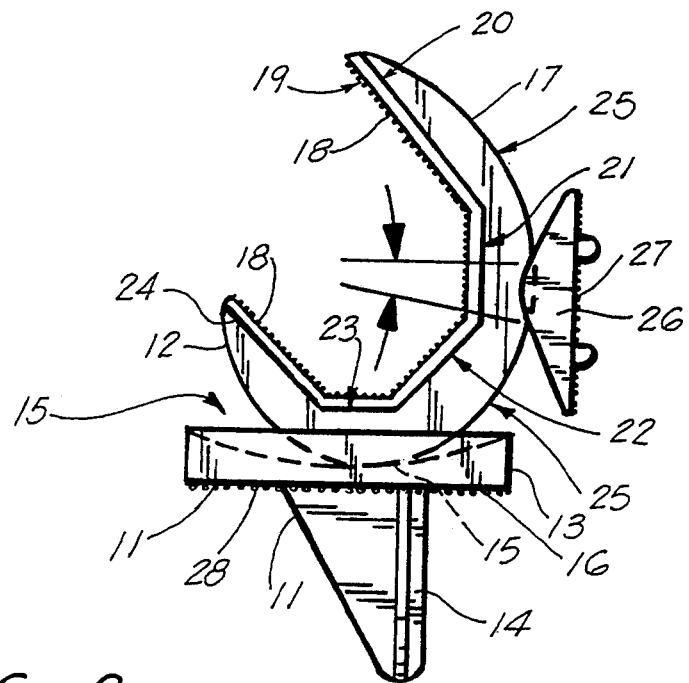
FIG. 2 is a side view of the preferred embodiment of the apparatus of the present invention showing relative angulation typical for stair climbing.

In FIG. 2, the preferred embodiment of the apparatus of the present invention (but showing a different angulation than Fig, 1) is designated generally by the numeral 10, The total knee prosthesis 10 includes a tibial component 11 and a femoral component 12. The tibial component 11 includes a tibial tray 13 and an optional fixation component 14 for improving surgical connection of the tibial component to the patient's tibia if needed. The tibial component includes a flat underside portion 16 and an upper concave articulating surface 15, The femoral component 12 provides a polymeric portion 17 and can optionally have a metallic or other rigid material as a backing member 18, A porous coating or surface texture 19 can also be employed to provide a tissue ingrowth surface, The metallic or rigid backing is defined by flat surfaces 20–24, Curved surface 25 defines a convex or Biconvex articulating surface that fits with the concave or Biconcave articulating surface 15 of the tibial component and is contoured to essentially mimic the surface of the intact knee femoral surfaces.

Patella component 26 is also preferably metallic, such as of a cobalt alloy or ceramic or ceramic-coated metal. The essentially hemispherical patella component 26 similarly can have a bone ingrowth surface 27. The patella component can be all metal, ceramic, or ceramic coated metal.

The following table lists the part numbers and part descriptions as used herein and in the drawings attached hereto.

| PARTS LIST | |
|---|---|
| Part number | Description |
| 3 | prior art knee prosthesis |
| 4 | metallic tibial component |
| 5 | fixation component |
| 6 | polymer insert |
| 7 | metallic femoral component |
| 8 | patella component |
| 9 | metallic backing |

| -continued | |
|---|---|
| PARTS LIST | |
| Part number | Description |
| 10 | knee prosthesis |
| 11 | tibial component |
| 12 | femoral component |
| 13 | tibial tray |
| 14 | fixation component |
| 15 | concave surface |
| 16 | flat undersurface |
| 17 | polymer portion |
| 18 | metallic backing |
| 19 | porous tissue ingrowth coating |
| 20 | flat surface |
| 21 | flat surface |
| 22 | flat surface |
| 23 | flat surface |
| 24 | flat surface |
| 25 | curved surface |
| 26 | patella component |
| 27 | porous ingrowth coating tissue |
| 28 | porous ingrowth coating |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:
1. A total knee prosthesis comprising:
 a) a bridged, near-anatomically shaped, bicondylar polymer femoral component having a pair of spaced, generally convex polymeric bearing surface of thickness greater than about six millimeters (6 mm) at articulating surface regions;
 b) a tibial component with a metallic bearing surface portion that includes concavities that receive the polymeric bearing surface of the femoral component during articulation of the femoral component upon the tibial component;
 c) a patella component with a metallic bearing surface portion that receives the polymer bearing surface of the femoral component during articulation of the femoral component upon the patella component; and
 d) a femoral attachment that enables the femoral component to be attached to the patient's femur.

2. The knee prosthesis of claim 1 wherein the polymer is an ultra high molecular weight polymer.

3. The knee prosthesis of claim 1 wherein the polymer is an ultra high molecular weight polyolefin.

4. The knee prosthesis of claim 1 wherein the polymer is an ultra high molecular weight polyethylene.

5. The knee prosthesis of claim 1 wherein the tibial and patella components are of a ceramic coated metal material.

6. The knee prosthesis of claim 1 wherein the tibial and patella components are of a ceramic material.

7. The knee prosthesis of claim 1 wherein the femoral component has a porous polymer coating portion for promoting bone ingrowth.

8. The knee prostheses of claim 1 wherein the femoral component contains a porous coated portion for improving bone cement attachment or promoting bone ingrowth.

9. The knee prosthesis of claim 8 wherein the femoral component has a metal bead coating for promoting bone ingrowth.

10. The knee prosthesis of claim 8 wherein the femoral component has a mesh coating for promoting bone ingrowth.

11. The knee prostheses of claim 1 wherein the tibial component contains a textured porous coating for promoting bone cement attachment or bone ingrowth.

12. The knee prosthesis of claim 11 wherein the tibial component has a metal bead coating for promoting bone ingrowth.

13. The knee prosthesis of claim 11 wherein the tibial component has a mesh coating for promoting bone ingrowth.

14. The knee prosthesis of claim 1 comprising a patella component that has a metallic bearing surface that articulates against the polymeric surface of the femoral component.

15. The knee prosthesis of claim 14 wherein the tibial component and patella component are each of a cobalt alloy.

16. The knee prosthesis of claim 1 wherein the femoral component has a metallic backing portion opposite the polymeric bearing surface.

17. The knee prosthesis of claim 16 wherein the backing is partial backing.

18. The knee prosthesis of claim 16 wherein the backing is a full backing that substantially covers the back side of the femoral component opposite the bearing surface of the femoral component.

19. The knee prosthesis of claim 1 wherein the polymer is a wear resistant polymer.

20. The knee prosthesis of claim 1 wherein the polymer is a creep resistant polymer.

21. A total knee prosthesis comprising:
   a) a bridged, near-anatomically shaped, bicondylar polymer femoral component having a pair of spaced, generally convex polymeric bearing surfaces of thickness greater than about six millimeters (6 mm) at articulating surface regions;
   b) a tibial component with a ceramic bearing surface portion that includes concavities that receive the polymeric bearing surface of the femoral component during articulation of the femoral component upon the tibial component;
   c) a patella component with a ceramic bearing surface portion that receives the polymeric bearing surface of the femoral component during articulation of the femoral component upon the patella component;
   d) femoral attachment means for enabling the femoral component to be attached to the patient's femur; and
   e) tibial attachment means for enabling the tibial component to be attached to the patient's tibia.

22. The knee prosthesis of claim 1 wherein the femoral component has a rigid backing portion opposite the polymeric bearing surface.

23. The knee prosthesis of claim 1 wherein the polymer has a carbon fiber reinforced polymer composite.

24. The knee prosthesis of claim 21 wherein the polymer of the femoral component is an ultra high molecular weight polymer.

25. The knee prosthesis of claim 21 wherein the polymer of the femoral component is an ultra high molecular weight polyolefin.

26. The knee prosthesis of claim 21 wherein the polymer of the femoral component is an ultra high molecular weight polyethylene.

27. The knee prosthesis of claim 21 wherein the tibial and patella components are of a ceramic coated metal material.

28. The knee prosthesis of claim 21 wherein the tibial and patella components are entirely of a ceramic material.

29. The knee prosthesis of claim 21 wherein the femoral component has a porous polymer coating portion for promoting bone ingrowth.

30. The knee prostheses of claim 21 wherein the femoral component contains a porous coated portion for improving bone cement attachment or promoting bone ingrowth.

31. The knee prosthesis of claim 30 wherein the femoral component has a metal bead coating for promoting bone ingrowth.

32. The knee prosthesis of claim 30 wherein the femoral component has a mesh coating for promoting bone ingrowth.

33. The knee prosthesis of claim 21 wherein the tibial component contains a textured porous coating for promoting bone cement attachment or bone ingrowth.

34. The knee prosthesis of claim 33 wherein the tibial component has a metal bead coating for promoting bone ingrowth.

35. The knee prosthesis of claim 33 wherein the tibial component has a mesh coating for promoting bone ingrowth.

36. The knee prosthesis of claim 21 comprising a patella component that has a metallic bearing surface that articulates against the polymeric surface of the femoral component.

37. The knee prosthesis of claim 36 wherein the tibial component and patella component are each of a cobalt alloy.

38. The knee prosthesis of claim 21 wherein the femoral component has a metallic backing portion opposite the polymeric bearing surface.

39. The knee prosthesis of claim 38 wherein the backing is partial backing.

40. The knee prosthesis of claim 38 wherein the backing is a full backing that substantially covers the back side of the femoral component opposite the bearing surface of the femoral component.

41. The knee prosthesis of claim 21 wherein the polymer is a wear resistant polymer.

42. The knee prosthesis of claim 21 wherein the polymer is a creep resistant polymer.

43. The knee prosthesis of claim 21 wherein the femoral component has a rigid backing portion opposite the polymeric bearing surface.

44. The knee prosthesis of claim 21 wherein the polymer has a carbon fiber reinforced polymer composite.

* * * * *